United States Patent
Wilder et al.

(10) Patent No.: US 9,878,165 B2
(45) Date of Patent: Jan. 30, 2018

(54) PATIENT PROGRAMMER HAVING A KEY-FOB-SIZED FORM FACTOR

(71) Applicant: Nuvectra Corporation, Plano, TX (US)

(72) Inventors: Steven E. Wilder, Ashland, OH (US); Michael S. Labbe, Twinsburg, OH (US); Jeff Gagnon, Champlin, MN (US); Ben Cottrill, Cleveland, OH (US)

(73) Assignee: Nuvectra Corporation, Plano, TX (US)

( * ) Notice: Subject to any disclaimer, the term of this patent is extended or adjusted under 35 U.S.C. 154(b) by 0 days.

(21) Appl. No.: 15/270,714

(22) Filed: Sep. 20, 2016

(65) Prior Publication Data
US 2017/0007839 A1    Jan. 12, 2017

Related U.S. Application Data

(63) Continuation of application No. 13/170,775, filed on Jun. 28, 2011.

(51) Int. Cl.
| | | |
|---|---|---|
| *A61N 1/36* | (2006.01) | |
| *A61N 1/372* | (2006.01) | |
| *A61N 1/378* | (2006.01) | |

(52) U.S. Cl.
CPC ....... *A61N 1/37247* (2013.01); *A61N 1/3787* (2013.01); *A61N 1/37229* (2013.01); *A61N 1/36071* (2013.01)

(58) Field of Classification Search
CPC .................. A61N 1/37247; A61N 1/37235
See application file for complete search history.

(56) References Cited

U.S. PATENT DOCUMENTS

| | | |
|---|---|---|
| 3,727,616 A | 4/1973 | Lenzkes |
| 5,342,408 A | 8/1994 | deCoriolis et al. |
| (Continued) | | |

FOREIGN PATENT DOCUMENTS

| | | |
|---|---|---|
| WO | WO 2005/105201 | 11/2005 |
| WO | WO 2009/134474 | 11/2009 |
| WO | WO 2010/111324 | 9/2010 |

OTHER PUBLICATIONS

Choi et al., "Hardware & Design & Compression Issues in Compact Bluetooth Enabled Wireless Telecardiology System," Interdisciplinary Program in Biomedical Engineering, Seoul National University, Feb. 13, 2006.

(Continued)

*Primary Examiner* — George Evanisko
(74) *Attorney, Agent, or Firm* — Haynes and Boone, LLP; Eric Li

(57) ABSTRACT

A patient programmer has a housing having a key-fob-sized form factor. The patient programmer has electrical circuitry implemented inside the housing. The electrical circuitry includes a communication module configured to conduct wireless communications with an implantable pulse generator. The patient programmer has a user display implemented on the housing. The user display is configured to display one or more statuses of the implantable pulse generator. The implantable pulse generator is configured to generate an electrical stimulation therapy. The patient programmer has one or more buttons implemented on the housing. The one or more buttons are configured to send instructions, via the communication module, to the implantable pulse generator to adjust a stimulation parameter of the electrical stimulation therapy.

20 Claims, 10 Drawing Sheets

(56) References Cited

U.S. PATENT DOCUMENTS

| | | |
|---|---|---|
| 5,383,915 A | 1/1995 | Adams |
| 5,626,630 A | 5/1997 | Markowitz et al. |
| 5,973,592 A | 10/1999 | Flick |
| 6,249,703 B1 | 6/2001 | Stanton et al. |
| 6,393,325 B1 | 5/2002 | Mann et al. |
| 6,516,227 B1 | 2/2003 | Meadows et al. |
| 6,553,263 B1 | 4/2003 | Meadows et al. |
| 6,662,052 B1 | 12/2003 | Sarwal et al. |
| 6,738,671 B2 | 5/2004 | Christopherson et al. |
| 6,820,019 B1 | 11/2004 | Kelly et al. |
| 6,842,647 B1 | 1/2005 | Griffith et al. |
| 7,177,690 B2 | 2/2007 | Woods et al. |
| 7,181,286 B2 | 2/2007 | Sieracki et al. |
| 7,203,549 B2 * | 4/2007 | Schommer ......... A61N 1/37229 607/60 |
| 7,209,790 B2 | 4/2007 | Thompson et al. |
| 7,272,445 B2 | 9/2007 | Phillips et al. |
| 7,330,762 B2 | 2/2008 | Boveja et al. |
| 7,359,751 B1 | 4/2008 | Erickson et al. |
| 7,369,897 B2 | 5/2008 | Boveja et al. |
| 7,389,147 B2 | 6/2008 | Wahlstrand et al. |
| 7,505,816 B2 | 1/2009 | Schmeling et al. |
| 7,515,044 B2 | 4/2009 | Welch et al. |
| 7,617,002 B2 | 11/2009 | Goetz |
| 7,647,117 B2 | 1/2010 | Bauhahn |
| 7,711,419 B2 | 5/2010 | Armstrong et al. |
| 7,729,766 B2 | 6/2010 | Toy et al. |
| 7,761,167 B2 | 7/2010 | Bennett et al. |
| 7,805,200 B2 | 9/2010 | Kast et al. |
| 8,170,681 B2 | 5/2012 | Jimenez et al. |
| 8,260,432 B2 | 9/2012 | DiGiore et al. |
| 8,346,361 B2 | 1/2013 | Bauhahn et al. |
| 8,401,663 B2 | 3/2013 | Aghassian |
| 8,401,664 B2 | 3/2013 | Chow et al. |
| 8,428,712 B2 | 4/2013 | Davis et al. |
| 8,447,411 B2 | 5/2013 | Skelton et al. |
| 8,463,392 B2 | 6/2013 | Aghassian |
| 8,473,066 B2 | 6/2013 | Aghassian et al. |
| 8,594,804 B2 | 11/2013 | Joshi |
| 2001/0007053 A1 | 7/2001 | Bardy |
| 2004/0064166 A1* | 4/2004 | Thompson ......... A61N 1/37252 607/60 |
| 2004/0133047 A1 | 7/2004 | Mazar et al. |
| 2004/0133079 A1 | 7/2004 | Mazar et al. |
| 2004/0193647 A1 | 9/2004 | Ueda et al. |
| 2005/0075693 A1 | 4/2005 | Toy et al. |
| 2005/0116840 A1 | 6/2005 | Simelius |
| 2005/0137480 A1 | 6/2005 | Alt et al. |
| 2005/0246006 A1* | 11/2005 | Daniels ............... A61N 1/0551 607/117 |
| 2006/0106431 A1 | 5/2006 | Wyler et al. |
| 2006/0140139 A1 | 6/2006 | DiSilvestro et al. |
| 2006/0241701 A1 | 10/2006 | Markowitz et al. |
| 2006/0247512 A1 | 11/2006 | Harwell et al. |
| 2006/0293607 A1 | 12/2006 | Alt et al. |
| 2007/0016090 A1 | 1/2007 | Brockway et al. |
| 2007/0049992 A1 | 3/2007 | Freeberg |
| 2007/0060979 A1 | 3/2007 | Strother et al. |
| 2007/0156207 A1 | 7/2007 | Kothandaraman et al. |
| 2007/0203545 A1 | 8/2007 | Stone et al. |
| 2007/0270921 A1 | 11/2007 | Strother et al. |
| 2008/0015656 A1 | 1/2008 | Gange et al. |
| 2008/0065182 A1 | 3/2008 | Strother et al. |
| 2008/0140163 A1* | 6/2008 | Keacher ............... G06F 19/3481 607/60 |
| 2008/0281217 A1 | 11/2008 | Peterson et al. |
| 2008/0300470 A1 | 12/2008 | Gerber et al. |
| 2009/0024178 A1 | 1/2009 | Hennig |
| 2009/0062778 A1 | 3/2009 | Gengtsson et al. |
| 2009/0076570 A1 | 3/2009 | Hoyme et al. |
| 2009/0118796 A1 | 5/2009 | Chen et al. |
| 2009/0149917 A1 | 6/2009 | Whitehurst et al. |
| 2010/0036445 A1 | 2/2010 | Sakai et al. |
| 2010/0036459 A1 | 2/2010 | Ramakrishnan et al. |
| 2010/0121408 A1 | 5/2010 | Imran et al. |
| 2010/0152817 A1 | 6/2010 | Gillbe |
| 2010/0204756 A1* | 8/2010 | Aghassian ......... A61N 1/37223 607/60 |
| 2010/0247071 A1 | 9/2010 | Mankovitz |
| 2010/0305663 A1 | 12/2010 | Aghassian |
| 2011/0046698 A1 | 2/2011 | Kivi et al. |
| 2011/0172738 A1 | 7/2011 | Davis et al. |
| 2011/0184491 A1 | 7/2011 | Kivi |
| 2011/0202103 A1* | 8/2011 | Wikman ............ A61N 1/37276 607/25 |
| 2012/0016439 A1 | 1/2012 | Alataris et al. |
| 2012/0119699 A1 | 5/2012 | Carbunaru et al. |
| 2012/0136413 A1* | 5/2012 | Bonde ................ A61N 1/36007 607/48 |
| 2012/0161945 A1 | 6/2012 | Single et al. |
| 2012/0165898 A1 | 6/2012 | Moffitt |
| 2012/0239118 A1 | 9/2012 | Ozawa et al. |
| 2012/0258756 A1 | 10/2012 | Pixley et al. |
| 2012/0277831 A1 | 11/2012 | Joshi |
| 2012/0290041 A1 | 11/2012 | Kim et al. |
| 2013/0004925 A1 | 1/2013 | Labbe et al. |
| 2013/0096653 A1 | 4/2013 | Winstrom |
| 2013/0165993 A1 | 6/2013 | Aghassian et al. |
| 2013/0193912 A1 | 8/2013 | Bornhoft |

OTHER PUBLICATIONS

Yuce et al., "A MICS Bank Wireless Body Sensor Network," The School of Electrical Eng. and Computer Science, The University of Newcastle, Callaghan, NSW 2308, Australia, and Electrical and Computer Eng. University of California, Santa Cruz, CA 65064-1077, USA, Jun. 4, 2007.

Yuce et al., "Implementation of Body Area Networks Based on MICS/WMTS Medical Bands for Healthcare Systems," The School of Electrical Eng. and Computer Science, The University of Newcastle, Callaghan, NSW 2308, Australia, 2008; 2008:3417-21.

Bradley, Peter, "An Ultra Low Power, High Performance Medical Implant Communication System (MICS) Transceiver for Implantable Devices," Zarlink Semiconductor (ULP Communications) Aug. 15, 2008.

Cho et al., A Planar MCIS Ban Antenna Combined With a Body Channel Communication Electrtode for Body Sensor Network, IEEE Transactions on Microwave Theory and Techniques, vol. 57, No. 1, Oct. 2009.

\* cited by examiner

PATIENT PROGRAMMER HAVING A KEY-FOB-SIZED FORM FACTOR

This is a continuation of U.S. application Ser. No. 13/170,775, filed Jun. 28, 2011. This disclosure is directed to a patient programmer for controlling an electrical stimulation implantable device.

FIELD OF THE INVENTION

Background

Neurostimulation devices deliver therapy in the form of electrical stimulation pulses to treat symptoms and conditions, such as chronic pain, Parkinson's disease, or epilepsy, for example. Implantable neurostimulation devices, for example, deliver neurostimulation therapy via leads that include electrodes located proximate to the muscles and nerves of a patient. Treatments frequently require two external devices: a neurostimulator controller and a neurostimulation device charger. Neurostimulator controllers are frequently used to adjust treatment parameters, select programs, and even to program treatment platforms into the implantable device. External neurostimulator device chargers are used to recharge batteries on the implanted device.

Conventional neurostimulator controllers are approximately the size of hand-held gaming system controllers, smartphones, or PDAs. While small, they are too large to comfortably be carried around in one's pocket and must be carried in a belt pouch or purse. Because of the size of these devices, they are not easily concealed and frequently result in unwanted attention. Known controllers provide so many features or functions that they sometimes overwhelm the patient to the point where the trial fails. A typical patient will only use a very small subset of the available features on the controllers. Most patients only use their controller to turn the neurostimulator on or off, select which neurostimulation program to run, and adjust their stimulation amplitude, while a very small percentage of patients utilize the advance controls to adjust program frequency and individual pulse/area stimulation parameters such as pulse width.

Existing chargers are typically about the same size as the neurostimulator controllers and are used for the sole purpose of recharging the implantable device's battery. These chargers are usually kept in the patient's house and used once a week or so depending upon stimulation parameters.

The present disclosure is directed to devices, systems, and methods that address one or more deficiencies in the prior art.

SUMMARY

This disclosure is directed to a system with dual patient controllers that control an implantable medical device. It includes a pocket controller and a separate integrated controller charger.

In one exemplary aspect, the present disclosure is directed to an integrated controller charger operable to both charge a rechargeable power source of an implantable medical device and control the implantable medical device. The controller charger includes a communication module configured to transmit information from the controller charger to the implantable medical device and configured to receive information from the implanted medical device. It also includes a power charging module configured to transmit energy storable at the rechargeable power source on the implantable medical device. A control module is configured to control both the communication module and the power charging module. The control module may include a processor and a memory and is operable to store the information received from the implanted medical device and generate signals to activate the stimulation programs on the implanted medical device.

In another exemplary aspect, the present disclosure is directed to an assembly for controlling an implantable medical device configured to transmit and receive information. The implantable medical device includes a rechargeable power source. The assembly includes a controller charger operable to both charge the implantable medical device and control the implantable medical device and includes a limited purpose controller sized smaller than the controller charger. The limited purpose controller includes a communication module configured to transmit information from the limited purpose controller to the implantable medical device and configured to receive information from the implanted medical device. It also includes a control module configured to transmit to and receive information from the communication module in communication with the implantable medical device. The controller may be configured to permit a user to control only a subset of the features controllable with the controller charger, including, for example, 1) electrical stimulation on/off selection, 2) stimulation program amplitude adjustment, and 3) electrical stimulation program selection.

In some exemplary aspects the assembly includes a controller charger operable to both charge the implantable medical device and control the implantable medical device. The controller charger includes a communication module configured to transmit information from the controller charger to the implantable medical device and configured to receive information from the implanted medical device. It also includes a power charging module configured to emit energy storable at the rechargeable power source on the implantable medical device. A control module interfaces with both the communication module and the power charging module. The control module is configured to permit a user to control features on the implantable medical device including a) electrical stimulation on/off selection, b) stimulation program amplitude adjustment, c) electrical stimulation program selection, and d) adjusting stimulation program frequency, as well as providing additional status information relating to the implanted medical device. The assembly also includes a limited purpose controller sized smaller than the controller charger. The limited purpose controller includes a communication module configured to transmit information from the controller to the implantable medical device and configured to receive information from the implanted medical device. It also includes a control module configured to transmit to and receive information from the implantable medical device. The limited purpose controller is configured to permit a user to control only a subset of the features controllable with the controller charger. The subset of the features includes 1) electrical stimulation on/off selection, 2) stimulation program amplitude adjustment, and 3) electrical stimulation program selection.

In another exemplary aspect, the present disclosure is directed to a method performed by a limited purpose controller in communication with an implanted implantable pulse generator. The method includes steps of receiving from the implantable pulse generator data representing enabled stimulation programs; storing the data representing the enabled stimulation programs on the limited purpose controller; receiving an input from a user to activate stimulation from the implantable pulse generator according to one of the enabled stimulation programs, the limited purpose controller being configured in a manner not permitting the user to modify the enabled stimulation program other than to adjust a global amplitude of pulses emitted by the implantable pulse generator according to an enabled stimulation program; and transmitting data representing the selected stimulation program from the limited purpose controller to the implantable pulse generator.

In another exemplary aspect, the present disclosure is directed to a method performed by a patient controller charger in communication with an implanted implantable pulse generator. The method includes steps of receiving from the implantable pulse generator data representing enabled stimulation programs; storing the data representing the enabled stimulation programs on the limited purpose controller; receiving an input from a user to adjust a frequency and pulse width of an electrical stimulation treatment; transmitting data representing the adjusted frequency and pulse from the patient controller charger to the implantable pulse generator; receiving an input from a user to charge a battery on an implanted implantable pulse generator with the patient controller charger; and emitting energy from the patient controller charger configured to charge the implantable pulse generator.

In another exemplary aspect, the present disclosure is directed to an integrated controller charger operable to both charge a rechargeable power source of an implantable medical device and control the implantable medical device. The controller charger includes a controller charger portion configured to wirelessly communicate with the implantable medical device, configured to receive inputs from a user, configured to send control signals indicative of the received inputs to the implantable medical device, and configured to receive information from the implantable medical device and display the information to a user. The controller charger also includes a coil portion configured to generate an inductive field to wirelessly charge a battery in the implantable medical device, and includes a flexible cable extending between and electrically connecting the controller charger portion and the coil portion, the flexible cable electrically connecting the controller charger and the coil portion.

In another exemplary aspect, the present disclosure is directed toward a pocket controller that is operable by a patient to adjust a plurality of operational parameters defining a stimulation program to be performed by an implantable medical device within the patient. The pocket controller includes a housing comprising a smaller form factor than a housing of a patient controller that offers a greater number of control options than the pocket controller. The pocket controller also communicates with the implantable medical device to adjust a plurality of the operational parameters of the implantable medical device. A number of the operational parameters that are adjustable with the pocket controller is less than a number of the operational parameters that are adjustable with the patient controller. A user interface is also provided to the pocket controller to receive input from the patient, allowing the patient to select, from the plurality of operational parameters adjustable with the pocket controller, a selected operational parameter that is to be adjusted by the patient using the pocket controller. The pocket controller also receives input from the patient indicating an adjustment to the selected operational parameter. The pocket controller also includes a communication module that is compatible with a receiver provided to the implantable medical device to transmit a signal indicative of the adjustment from the pocket controller to the implantable medical device and receive information from the implantable medical device. A control module including a processor is configured to convey the signal indicative of the adjustment entered via the user interface to the communication module to be transmitted to the implantable medical device.

In another exemplary aspect, the present disclosure is directed toward a system for treating a patient. The system includes an implantable medical device that is to be implanted in the patient to execute an internal treatment routine on the patient, the internal treatment routine being governed by a plurality of operational parameters. A patient controller is provided to communicate with the implantable medical device and is to be placed in possession of the patient to allow the patient to adjust a plurality of the operational parameters while the implantable medical device is implanted in the patient. A pocket controller that communicates with the implantable medical device and is also to be placed in possession of the patient. The pocket controller includes a smaller form factor than a form factor of the patient controller and is usable by the patient to adjust a plurality of, but less than all of the operational parameters that are adjustable with the patient controller. The pocket controller includes a user interface that is usable by the patient to select, from the plurality of operational parameters, a selected operational parameter that is to be adjusted by the patient using the pocket controller, and to input or select an adjustment to the selected operational parameter.

In another exemplary aspect, the present disclosure is directed toward a system for treating a patient. The system includes an implantable electrical stimulation device that is to be implanted in the patient that executes an electrical stimulation program to be performed on the patient. The electrical stimulation program is governed by a plurality of operational parameters. A patient controller is provided to communicate with the implantable electrical stimulation device and is to be placed in possession of the patient to allow the patient to adjust the plurality of operational parameters while the implantable electrical stimulation device is implanted in the patient. The plurality of operational parameters adjustable via the patient controller include an amplitude of an individual electrical pulse emitted as part of a stimulation program performed by the implantable electrical stimulation device relative to an amplitude of another electrical pulse to be emitted as part of the same stimulation program performed by the implantable electrical stimulation device. A pocket controller is also provided to communicate with the implantable electrical stimulation device and is to be placed in possession of the patient. The pocket controller has a smaller form factor than a form factor of the patient controller. The pocket controller is usable by the patient to adjust a plurality of, but less than all of the operational parameters that are adjustable with the patient controller. One of the operational parameters adjustable via the pocket controller includes a global amplitude of electrical pulses in a series of electrical pulses to be emitted by the implantable electrical stimulation device as part of a stimulation program. The pocket controller further includes a user interface that is usable by the patient to input an adjustment of each of the plurality of operational parameters, and a display device. The display device displays at least one of a status of a battery provided to power the implantable electrical stimulation device, a status of a battery provided to power the pocket controller, an operational status of the implantable electrical stimulation device, and information concerning one or more of the operational parameters.

In another exemplary aspect, the present disclosure is directed toward a method of familiarizing a patient with a programmer for controlling execution of a treatment routine to be performed on the patient, where the treatment routine is governed by a plurality of operational parameters. The method includes providing the patient with a first pocket controller that communicates with a temporary, trial electrical stimulation device supported externally of the patient during a trial period to perform the treatment routine. The trial period is to determine whether the treatment routine performed by the external electrical stimulation device is beneficial to the patient. In response to a determination that the treatment routine is beneficial to the patient, the method includes establishing communication between the first pocket controller and an implanted electrical stimulation device or establishing communication between a second pocket controller, which is substantially-similar to the first pocket controller, and the electrical stimulation device to allow the first or second pocket controllers to change a plurality of the operational parameters. Communications are also established between a patient controller to be provided to the patient and the internal electrical stimulation device to change a greater number of the operational parameters than a number of the operational parameters that are adjustable using the first or second pocket controllers.

Note that U.S. patent application Ser. No. 13/170,558, titled "KEY FOB CONTROLLER FOR AN IMPLANTABLE NEUROSTIMULATOR" and filed on the same day as the present application and is incorporated herein in its entirety by reference.

BRIEF DESCRIPTION OF THE DRAWINGS

Aspects of the present disclosure are best understood from the following detailed description when read with the accompanying figures.

DETAILED DESCRIPTION

Figure 1A:
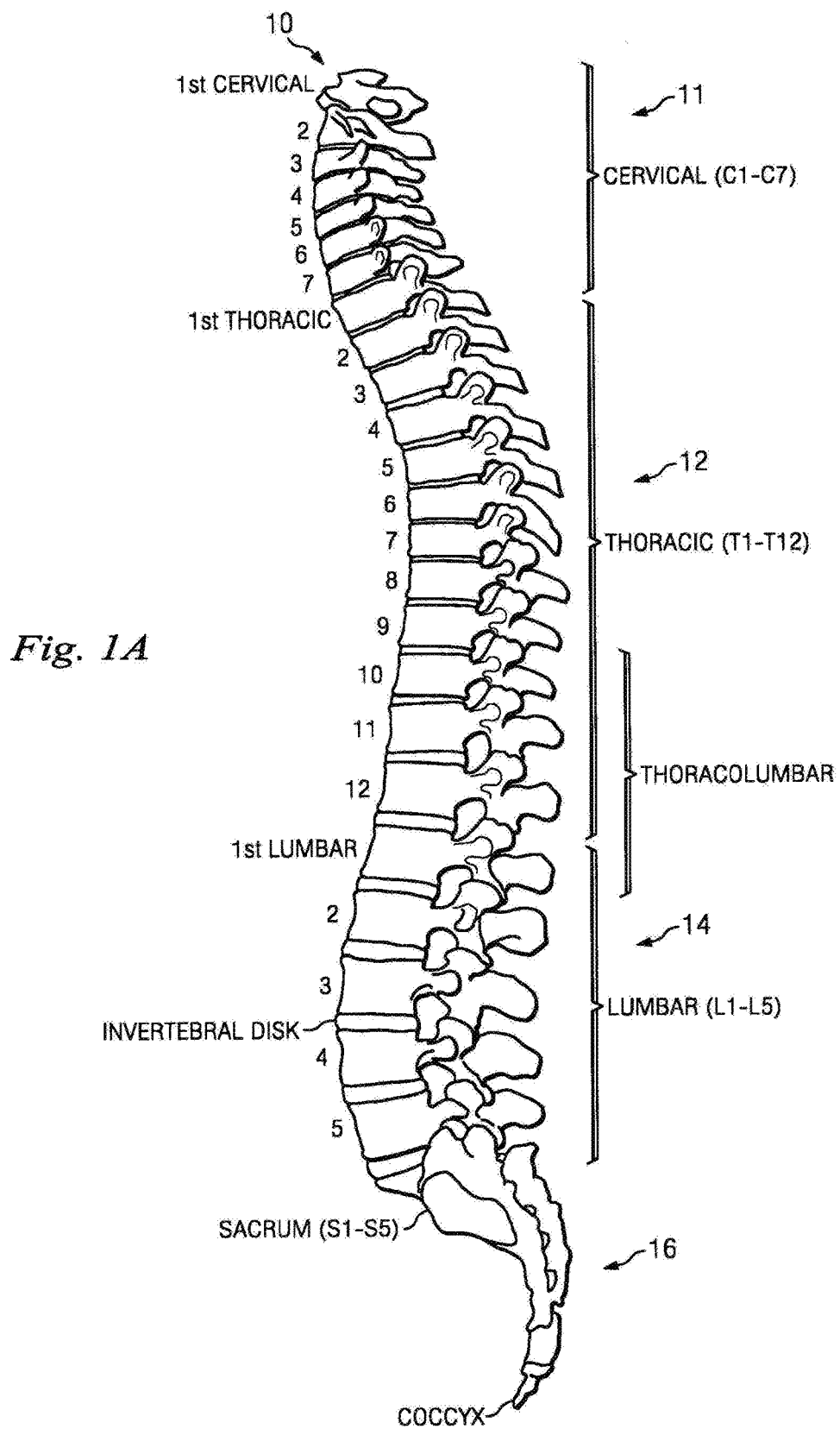
FIGS. 1A and 1B are illustrations of a patient's spine with an exemplary electrical stimulator treatment system disposed to treat a particular region of the spine in accordance with one aspect of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The devices, systems, and methods described herein introduce an improved way for controlling and charging an implanted medical device. They use a dual controller system that includes a pocket controller and a separate controller charger. The most-used functions of an electrical stimulator's controller are incorporated into a small, thin pocket controller that is not only comfortable to carry in a pocket, but can also be attached to a key ring, lanyard, or other such carrying device for ease of daily use. These most-used functions are a subset of features commonly found on an electrical stimulator's controller, and include features such as turning the electrical stimulation on and off, selecting which electrical stimulation program to run, and adjusting the stimulation amplitude. By limiting the functions of this device to those most commonly used on a daily basis, the device becomes much less intimidating to the patient thereby increasing patient compliance, and the size of the device is substantially reduced, rendering it less obtrusive and therefore making the patient more comfortable with having and using an implanted electrical stimulator.

In addition, the devices, systems, and methods described herein introduce a separate patient controller charger for the implanted medical device that provides advanced control features and includes an integrated charger for the implantable power source. Since the advanced features are necessary only for performing periodic (non-daily) maintenance or stimulation adjustment, and performing other less frequently required functions, these advanced features, including the subset features for redundancy, are maintained on a device separate and apart from the pocket controller. These features are integrated with the also-infrequently used charger for the implantable power source. Therefore, where a conventional charger performs only a function of charging the implant's battery and may include powering stimulation on and off, the system disclosed herein includes a multi-function, full-featured advance patient controller charger combination. In the embodiment shown, patient controller charger incorporates a full color graphical user interface with touch screen that presents a simplistic, but rich feature set for the more advanced, while maintaining the charging functions. Since the larger-sized patient controller charger can be left at home, its larger size (approximate size of a PDA) will not raise undesired interest from others. Users have the smaller unobtrusive pocket controller to take with them when they are on the go, and have comfort of the advanced features available for use when in the privacy of their home.

Further, the dual patient controllers disclosed herein provide a level of redundancy and risk management not achieved with a single controller. For example, if one controller malfunctions or is misplaced, a patient can still use the second controller for important control functions until the malfunctioning or misplaced controller is replaced. Accordingly, the patient can continue with his or her scheduled therapy, select another program as desired for effectiveness, and control the stimulation amplitude in the event that it becomes painful or undesired.

As used herein, the term "stimulation program" refers to a series of one or more stimulation pulses having a defined relationship used to treat a specific therapy or condition. A modification to the stimulation program involves adding or removing a pulse from the program, or changing the defined relationship of one pulse relative to the next pulse, but does not include adjusting the pulse amplitude or the pulse width of individual pulses or the series of pulses. According to alternate embodiments, the pulse amplitude and/or the pulse width of individual pulses or the series of pulses can optionally be adjusted using a full-feature controller such as the patient controller, but can not be adjusted using the pocket controller.

Figure 1B:
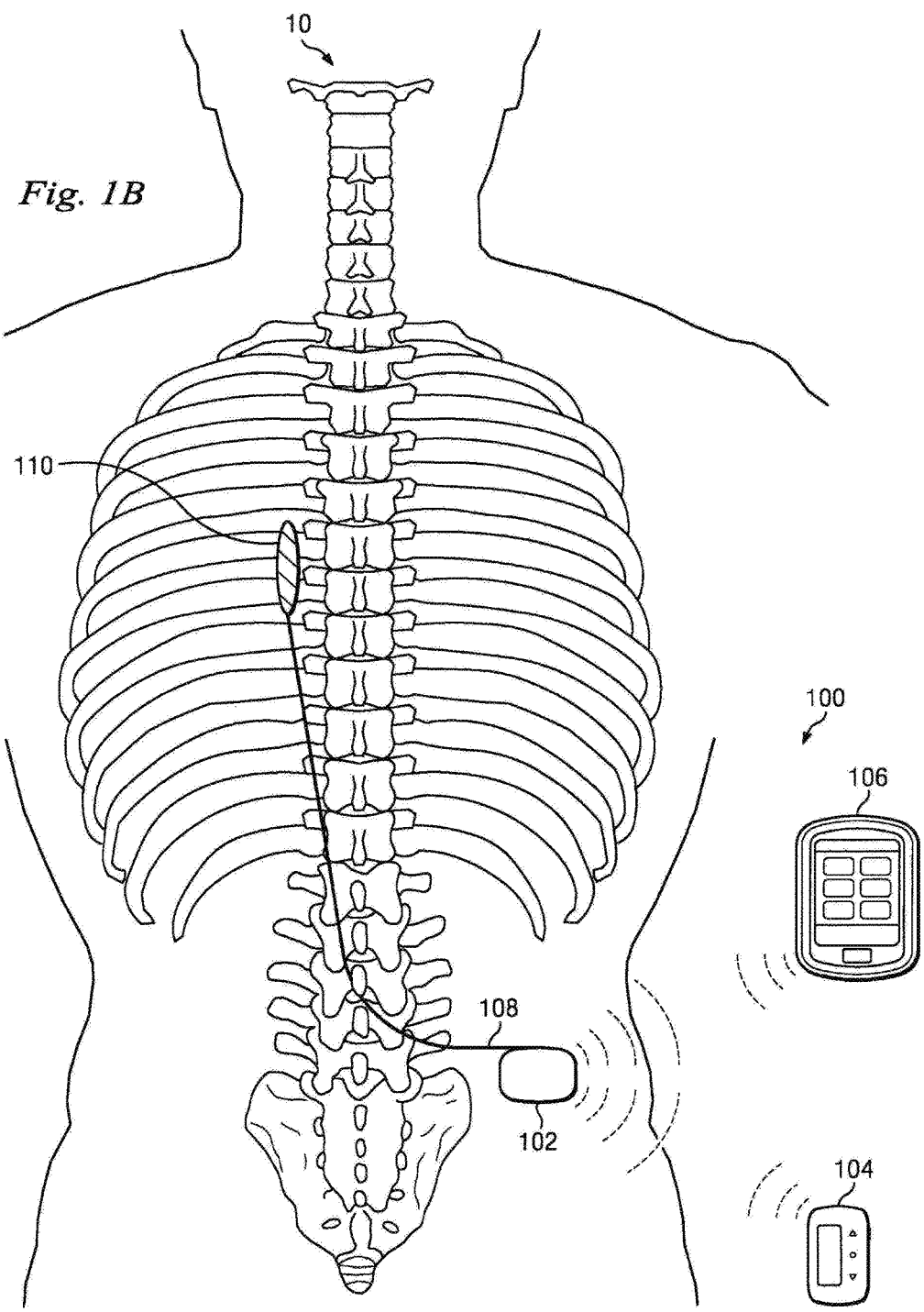

FIG. 1A is a side view of a spine 10, and FIG. 1B is a posterior view of the spine 10. FIG. 1B shows an exemplary electrical stimulator treatment system 100 disposed to treat a spinal region for treating a symptom, such as chronic pain. The system includes an implantable pulse generator (IPG) 102 that delivers electrical stimulation therapy to the patient, and dual patient controllers shown and described as a pocket controller 104 and a patient controller charger (PPC) 106.

Referring now to FIGS. 1A and 1B, the spine 10 includes a cervical region 11, a thoracic region 12, a lumbar region 14, and a sacrococcygeal region 16. The cervical region 11 includes the top seven vertebrae, which may be designated with C1-C7. The thoracic region 12 includes the next twelve vertebrae below the cervical region 11, which may be designated with T1-T12. The lumbar region 14 includes the final five "true" vertebrae, which may be designated with L1-L5. The sacrococcygeal region 16 includes nine fused vertebrae that make up the sacrum and the coccyx. The fused vertebrae of the sacrum may be designated with S1-S5.

Neural tissue (not illustrated for the sake of simplicity) branches off from the spinal cord through spaces between the vertebrae. The neural tissue, along with the cord itself, can be individually and selectively stimulated in accordance with various aspects of the present disclosure. For example, referring to FIG. 1B, the IPG 102 is implanted inside the body. A conductive lead 108 is electrically coupled to the circuitry inside the IPG 102. The conductive lead 108 may be removably coupled to the IPG 102 through a connector, for example. A distal end of the conductive lead 108 is attached to one or more electrodes 110. In the example shown, the electrodes 110 are implanted adjacent to a desired nerve tissue in the thoracic region 12. The distal end of the lead 108 with its accompanying electrodes may be positioned beneath the dura mater using well-established and known techniques in the art.

The electrodes 110 deliver current drawn from the IPG 102, thereby generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, bladder control, weight control or regulation of heart beats.

It is understood that the IPG 102, the lead 108, and the electrodes 110 may be implanted completely inside the body, may be positioned completely outside the body or may have only one or more components implanted within the body while other components remain outside the body. When they are implanted inside the body, the implant location may be adjusted (e.g., anywhere along the spine 10) to deliver the intended therapeutic effects of spinal cord electrical stimulation in a desired region of the spine. The IPG 102 in this system is a fully implantable, battery-powered neurostimulation device for providing electrical stimulation to a body region of a patient. In the example shown in FIG. 1B, the IPG 102 is configured to provide neural stimulation to the spine. However, in other embodiments, IPG 102 may be a different type of pulse generator, including, for example, a pacemaker, a defibrillator, a trial stimulator or any other type of medical device. Here, the IPG 102 is structurally configured and arranged for wireless programming and control through the skin of the patient. Accordingly, it includes a transmitter and receiver capable of communicating with external programming and control devices, such as the pocket controller 104, the PPC 106, and a separate clinician programmer (not shown). It also includes a rechargeable power source, such as a battery configured to be wirelessly recharged through the patient's skin when the PPC 106 is externally placed in the proximity of the IPG 102.

Figure 2:
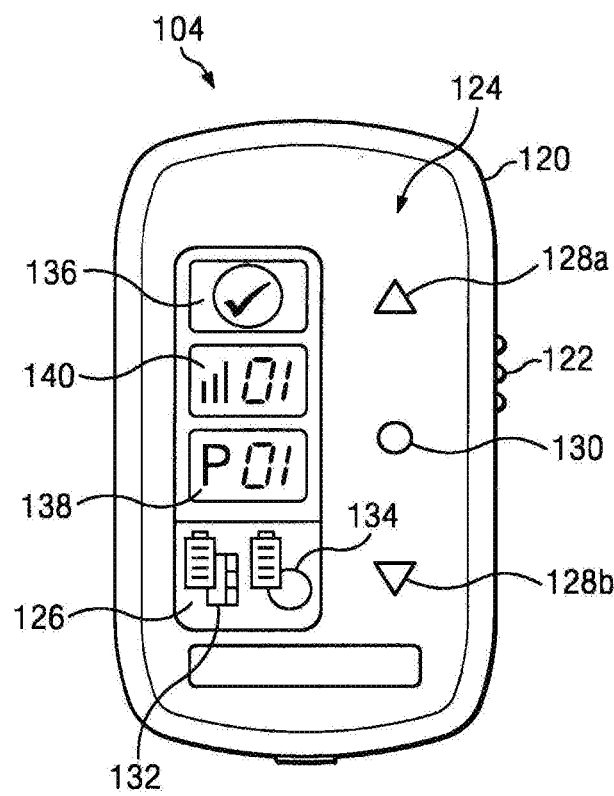
FIG. 2 is an illustration of an exemplary pocket controller in accordance with one aspect of the present disclosure.
Figure 3:
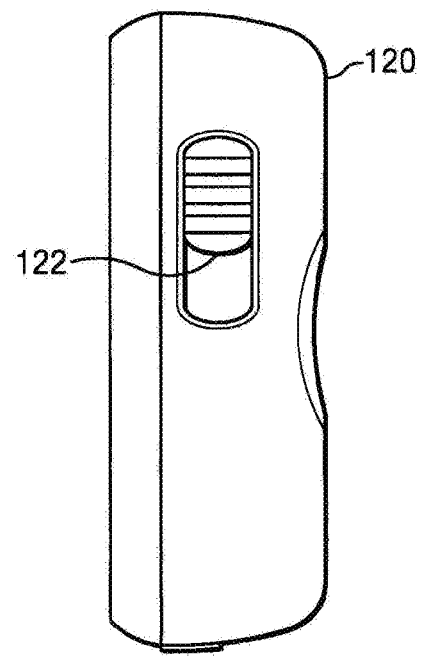
FIG. 3 is an illustration of a side of the exemplary pocket controller of FIG. 2 in accordance with one aspect of the present disclosure.
Figure 4:
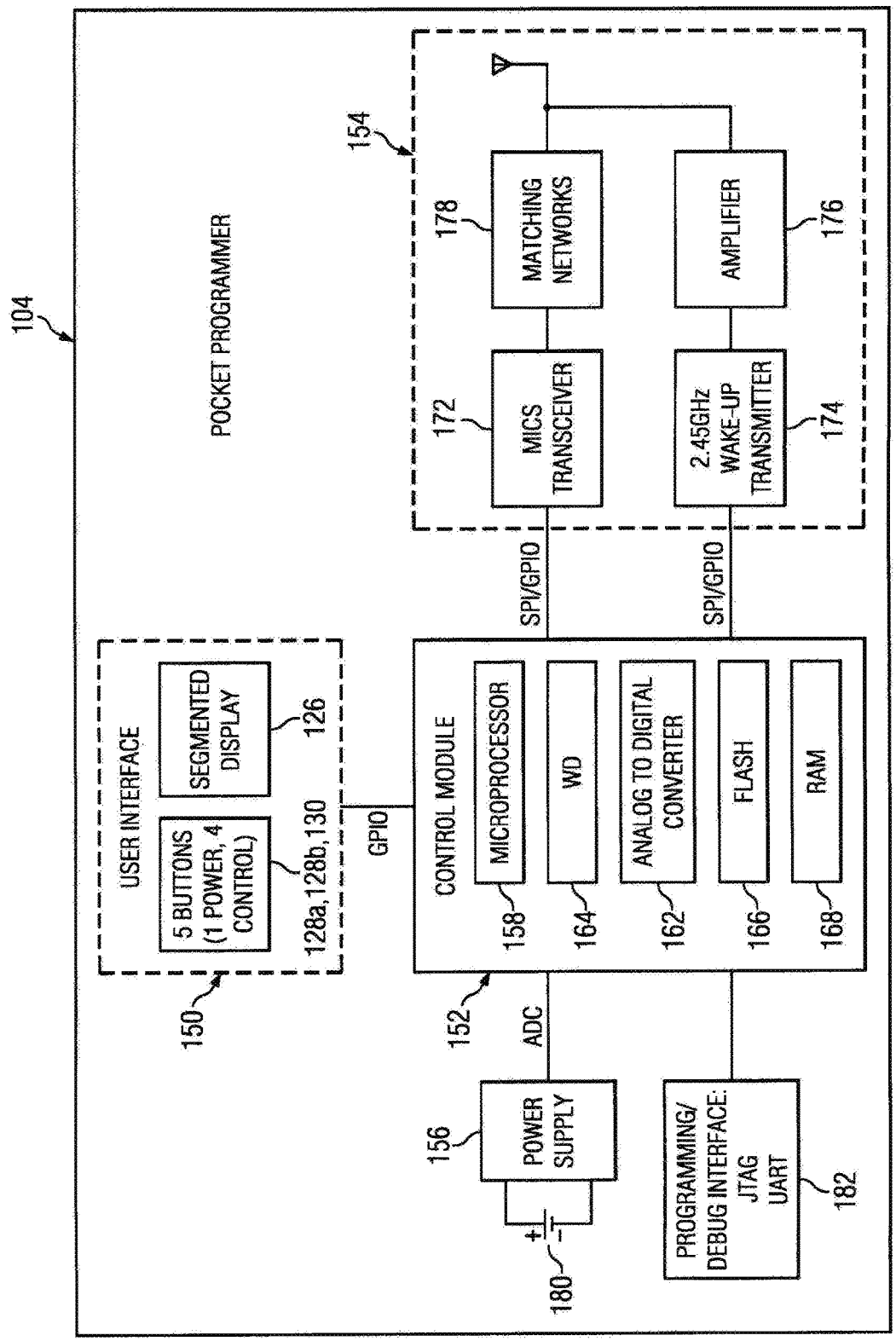
FIG. 4 is block diagram of components of the exemplary pocket controller of FIG. 2 in accordance with one aspect of the present disclosure.

The pocket controller 104 provides only limited functionality for controlling the IPG 102, and allows a user to control the most-used, such as daily-used, functions of the IPG 102. It is sized and configured for simple convenience and discreetness. The PPC 106 performs all the functions of the pocket controller 104, but also includes more advanced features and functionality for controlling the IPG 102 that are used less frequently than a daily basis, such as, for example, perhaps weekly. In addition, it is an integrated charger for recharging the power source in the IPG 102. The PPC 106 can be left at home, as its functions are typically not required for daily use. A separate clinician programmer (not shown) is a device typically maintained in a health care provider's possession and can be used to program the IPG 102 during office visits. For example only, the clinician controller can define the available stimulation programs for the device by enabling and disabling particular stimulation programs, can define the actual stimulation programs by creating defined relationships between pulses, and perform other functions. FIGS. 2-4 show the pocket controller 104 in greater detail and FIGS. 5-9 show the PPC 106 in greater detail.

Turning first to FIGS. 2 and 3, the pocket controller 104 comprises an outer housing 120 having an on-off switch 122, a plurality of control buttons 124, and a display 126. In this embodiment, the housing 120 is sized for discreetness and may be sized to fit easily in a pocket and may be about the same size as a key fob. In one example, the housing 120 forming the pocket controller 104 has a thickness of less than about 1.5 inch, a width of less than about 1.5 inch, and a height of less than about 3 inches. In another example, the housing 120 forming the pocket controller 104 has a thickness of about 0.8 inch, a width of about 1.4 inch, and a height of about 2.56 inch. However, both larger and smaller sizes are contemplated.

In this example, the control buttons 124 include two adjustment buttons 128a, 128b, a select button 130, and an emergency off button (not shown, but disposed on a side of the housing 120 opposing the on-off switch 122). The two adjustment buttons 128a, 128b allow a user to scroll or highlight available options and increase or decrease values shown on the display 126. The select button 130 allows a user to enter the value or select the highlighted options. In this example, the buttons 128a, 128b are used to navigate to one of the three available functions: 1) electrical stimulation on/off, 2) control stimulation amplitude adjustment, and 3) electrical stimulation program selection. Once the desired function is highlighted, the select button is pushed to allow changes (i.e. change the stimulation amplitude, select a different stimulation program, or turn the electrical stimulation on or off). In some examples, the IPG control functions of the pocket controller 104 consist of these functions. The emergency off button is disposed for easy access for a patient to turn off stimulation from the IPG 102 if the IPG provides too much stimulation or stimulation becomes uncomfortable for the patient.

In the embodiment shown, the display 126 is an LCD display arranged to convey information to the user regarding selectable options, present settings, operating parameters and other information about the IPG 102 or the pocket controller 104. In this example, the display 126 shows the pocket controller's battery status at 132, the IPG's battery status at 134, the IPG's on or off status at 136, the currently selected electrical stimulation program at 138, and the amplitude setting of the running electrical stimulation program at 140. Other types of displays are also contemplated.

FIG. 4 shows a block diagram of components making up the pocket controller 104. It includes a user interface 150, a control module 152, a communication module 154, and a power storing controller 156. The user interface 150 is comprised of the buttons 128a, 128b, 130 and the display 126 described above with reference to FIG. 2.

As can be seen, the user interface 150 is in communication with the control module 152. The control module 152 comprises a processor 158, memory, an analog-digital converter 162, and a watch dog circuit 164. The processor 158 may include a microprocessor, a controller, a digital signal processor (DSP), an application specific integrated circuit (ASIC), a field programmable gate array (FPGA), discrete logic circuitry, or the like. The processor 158 is configured to execute code or instructions provided in the memory. Here, the memory is comprised of flash memory 166 and RAM memory 168. However, the memory may include any volatile or non-volatile media, such as a random access memory (RAM), read only memory (ROM), non-volatile RAM (NVRAM), electrically erasable programmable ROM (EEPROM), flash memory, and the like. In some embodiments, the memory stores sets of stimulation control parameters that are available to be selected for delivery through the communication module 154 to the IPG 102 for electrical stimulation therapy. The AD converter 162 performs known functions of converting signals and the WD 164 is arranged to time out when necessary, such as in an event where the software becomes stuck in a loop. In one embodiment, the control module 152 comprises integrated circuits disposed on a PC board.

The communication module 154 comprises a medical implant communication service (MICS) RF transceiver 172 used to communicate with the IPG 102 to communicate desired changes and to receive status updates from and relating to the IPG 102, such as battery status and any error information. In this example, the MICS RF transceiver 172 utilizes a loop antenna for the communications with the IPG 102. Other antennas, such as, for example, dipole, chip antennas, or other known in the art also may be used. The communication module 154 also includes a wake up transmitter 174, an amplifier 176, and matching networks 178. The wake up transmitter 174 operates on a high frequency and is configured to send a short signal burst to wake up the IPG 102 when it is in a power-saving mode. Once the IPG 102 is ready, a communications link can be established between the IPG 102 and pocket controller 104, and communications can then occur over the MICS transceiver 172 using a standard frequency for a medical device transmission. The matching networks 178 tunes the antenna for optimum transmission power for the frequency selected. The pocket controller 104 also includes a programming interface 182. This may be used during manufacturing to load an operating system and program the pocket controller 104.

The power storing controller 156 is configured to convert power to recharge one or more rechargeable batteries 180. The batteries 180 provide power to operate the pocket controller 104 allowing it to receive user inputs and transmit control signals to the IPG 102. Some embodiments use primary cell batteries instead of rechargeable batteries. As indicated above, this pocket controller 104 is part of a larger system that contains the PPC 106 with a rich feature set for controlling the IPG 102 and includes an integrated battery charger used to charge the IPG's battery. By providing both the pocket controller 104 and the PPC 106, the patient can have a small unobtrusive device to carry around as they go about their daily business and a larger more full featured device which they can use in the comfort and privacy of their homes.

The pocket controller 104 is not only comfortable to carry in a pocket, but can also be attached to a key ring, lanyard, or other such carrying device for ease of daily use. Its functions are a subset of functions found on the PPC 106, and permit a user to power the IPG on and off (i.e., the IPG 102 remains on, but stimulation is toggled between the on state when the IPG 102 is emitting electrical pulses and the off state when the IPG 102 is not emitting electrical pulses but remains in the standby mode for additional communications from the pocket controller 104, the PPC 106, or both), select which electrical stimulation program to run, and adjust their stimulation amplitude. By limiting the functions of the pocket controller to those most commonly used on a daily basis, the device becomes much less intimidating to the patient, and allows it to be kept very small. By keeping the device small, such as about key fob size, it becomes unobtrusive and the patient is more comfortable with having and using an implanted device.

Figure 5:
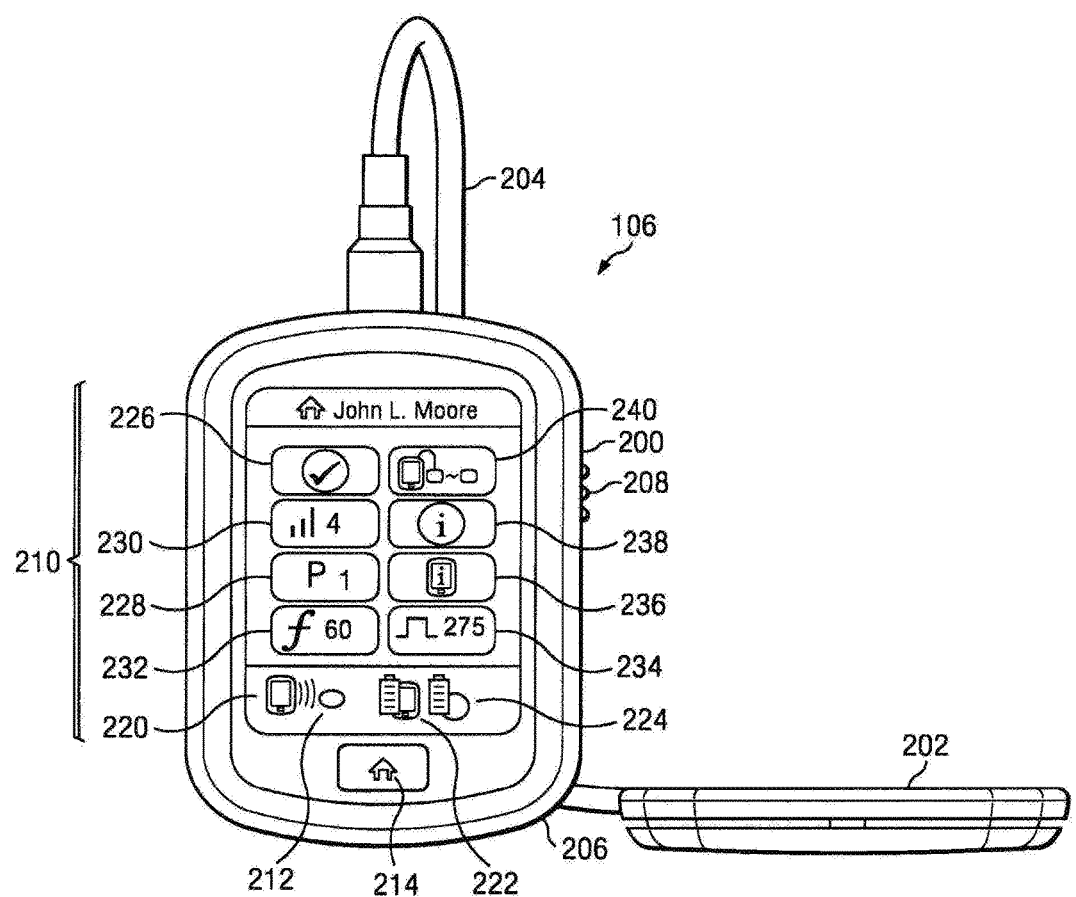
FIG. 5 is an illustration of an exemplary patient controller charger in accordance with one aspect of the present disclosure.
Figure 6:
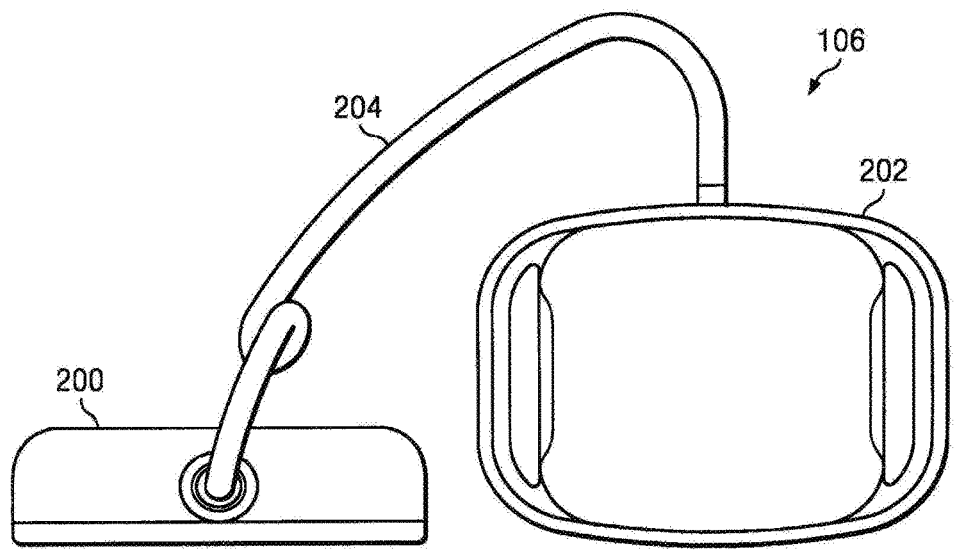
FIG. 6 is an illustration of a top view of the exemplary patient controller charger of FIG. 5 in accordance with one aspect of the present disclosure.
Figure 7:
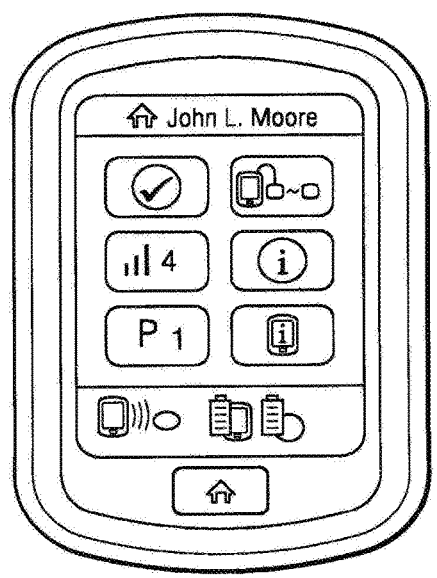
FIG. 7 is an illustration of an exemplary alternatively programmed patient controller charger in accordance with one aspect of the present disclosure.

FIGS. 5-7 show the PPC 106 in greater detail. FIG. 5 is a front view of the PPC and FIG. 6 is a top view of FIG. 5. Referring to FIGS. 5-7, the PPC 106 performs all the same operating functions as the pocket controller 104, but includes additional operating functions making it a multi-function full-featured, advanced patient controller charger. In the embodiment shown, the PPC 106 provides a simple but rich feature set to the more advanced user, along with the charging functions.

The PPC 106 includes a controller-charger portion 200 and a coil portion 202 connected by a flexible cable 204 and sharing components as described below. The controller-charger portion 200 comprises an outer housing 206 having an on-off switch 208 on its side, a plurality of control buttons 210, and a display 212, and an emergency off button (not shown, but disposed on a side of the housing 206 opposing the on-off switch 208). In this embodiment, the control buttons 210 are icons on the display 212, and the display is a full color, touch screen, graphical user interface. In addition, the controller-charger portion 200 includes a home button 214 configured to return the displayed images to a home screen. The controller-charger portion 200 is larger than the pocket controller 104 and in one embodiment is sized with a height greater than about 3 inches, a width greater than about 2.5 inches, and a thickness greater than about 0.8 inch. In another embodiment, the controller-charger portion is sized with a width of about 3.1 inches, a height of about 4.5 inches, and thickness of about 0.96 inches, although both larger and smaller sizes are contemplated.

In this example, the control buttons 210 allow a user to select a desired feature for control or further display. Particularly, the control buttons 210 enable functions of the PPC 106 that are the same as those of the pocket controller 104 (stimulation on/off, program stimulation amplitude adjustment, and stimulation program selection) along with additional features including: charging IPG battery, individual pulse stimulation amplitude adjustment, stimulation program frequency adjustment, individual pulse width adjustment, detailed IPG status, detailed PPC status, PPC setup/configuration, a PPC battery status indicator, PPC to IPG communication status indicator, and other items and functions. The detailed IPG status may include, for example, IPG serial number and IPG software revision level. Detailed PPC status may include, for example, date and time setting, brightness control, audio volume and mute control, and PPC serial number and software revision level.

By having a pocket controller that includes only three controls (stimulation on/off, program amplitude adjust, and stimulation program selection), a user can quickly and easily identify and select the features that are most commonly used. Features that are used less frequently, such as IPG recharge, are only included on the full-featured PPC. Features that are seldom accessed, or not accessed at all by some users, including individual pulse amplitude adjust, pulse width adjust, stimulation program frequency adjust, or serial number and software revision information, are also not included on the limited-feature pocket controller, but are included on the PPC. This allows the pocket controller to be significantly smaller, with a very simple and easy to user interface, as compared to systems that need to support all of these features.

Referring to the example shown in FIG. 5, the touch screen display 212 is arranged to convey information to the user regarding selectable options, current settings, operating parameters and other information about the IPG 102 or the PPC 106. In this example, the display 212 shows a MICS communication indicator 220, the PPC's battery status at 222, the IPG's battery status at 224, the IPG's on or off status at 226, the currently selected electrical stimulation program at 228, and the amplitude setting of the active electrical stimulation program at 230. In addition, the display 212 shows the frequency 232, the pulse width setting 234, a selectable status icon for accessing detailed PPC information 236, a selectable status icon for accessing detailed IPG information 238, and a selectable icon for enabling IPG charging 240. Selecting any single icon may activate another menu within that selected subject area. The controller-charger portion 200 may include a rechargeable battery whose charge status is shown by the PPC's battery status at 222.

The coil portion 202 is configured to wirelessly charge the batteries in the IPG 102. In use, the coil portion 202 is applied against the patient's skin externally so that energy can be inductively transmitted and stored in the IPG battery. As noted above, the coil portion 202 is connected with the integrated controller-charger portion 200. Accordingly, the controller-charger portion 200 can simultaneously display the current status of the coil portion 204, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

FIG. 7 shows an alternative display configuration of the PPC 106, including fewer available functions for user control. In this embodiment, the user has been denied access to the frequency and pulse width buttons shown in FIG. 5. Accordingly, in some examples, the health care provider may program the IPG 102 with the clinician controller (not shown) so that the IPG 102 allows the PPC 106 to control certain parameters as in the device in FIG. 5 or may program the IPG 102 to deny control of certain parameters from the PPC 106 as in the device in FIG. 7. In FIG. 7, the absence of the buttons indicates that those options are not available.

Figure 8:
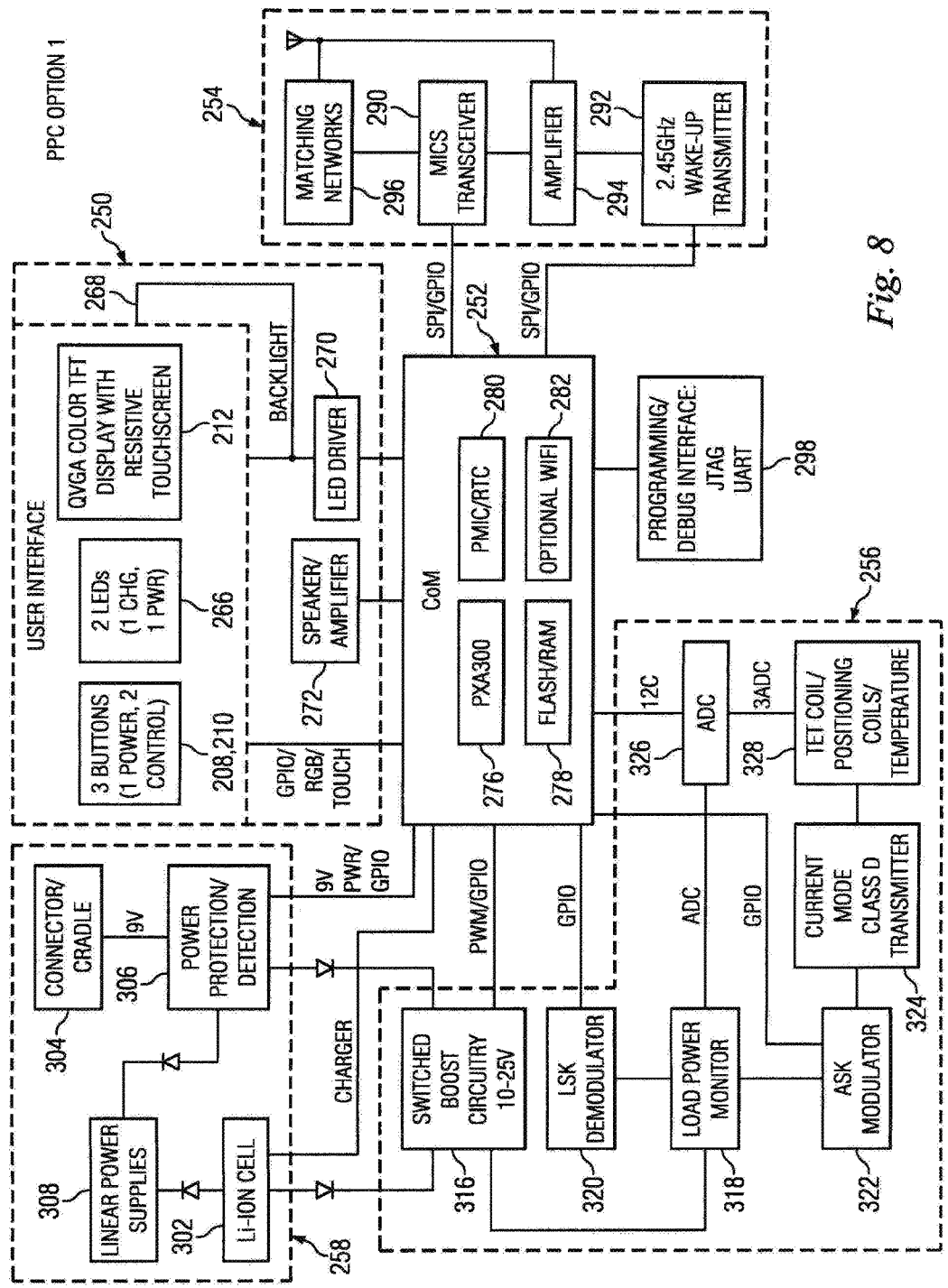
FIG. 8 is block diagram of components of the exemplary patient controller charger of FIGS. 5-7 in accordance with one aspect of the present disclosure.

FIG. 8 shows a block diagram of the components making up the PPC 106. It includes a user interface 250, a control module 252, a communication module 254, an IPG power charging module 256, and a power storing module 258. The user interface 250 is comprised of the buttons 210 and the display 212 described above. In this embodiment however, the user interface 250 also includes one or more LEDs 266 signifying whether the PPC 106 is charging or powered on and a backlight 268 that illuminates the color display. In some embodiments, these LEDs may have colors symbolizing the occurring function. An LED driver 270 and a speaker or amplifier 272 also form a part of the user interface 250.

As can be seen, the user interface 250 is in communication with the control module 252. The control module 252 comprises a processor 276, memory 278, and a power management integrated circuit (PMIC)/real time clock (RTC) 280. In the example shown, the control module 252 also includes a Wi-Fi RF transceiver 282 that allows the PPC 106 to connect to a wireless network for data transfer. For example, it may permit doctor-patient interaction via the internet, remote access to PPC log files, remote diagnostics, and other information transfer functions. The PMIC 280 is configured to control the charging aspects of the PPC 106. The Wi-Fi transceiver 282 enables Wi-Fi data transfer for programming the PPC 106, and may permit wireless access to stored data and operating parameters. Some embodiments also include a Bluetooth RF transceiver for communication with, for example, a Bluetooth enabled printer, a keyboard, etc.

In one embodiment, the control module 252 also includes an AD converter and a watch dog circuit as described above with reference to the control module 252. Here, the memory 278 is comprised of flash memory and RAM memory, but may be other memory as described above. In some embodiments, the processor 276 is an embedded processor running a WinCE operating system (or any real time OS) with the graphics interface 250, and the memory 278 stores sets of stimulation control parameters that are available to be selected for delivery through the communication module 254 to the IPG 102 for electrical stimulation therapy. In one embodiment, the control module 252 comprises integrated circuits disposed on a PC board.

The communication module 254 comprises a MICS RF transceiver 290, a wake up transmitter 292, an amplifier 294, and matching networks 296. The communication module 254 may be similar to the communication module 154 discussed above, and will not be further described here. The PPC 206 also includes a programming interface 298 that may be used during manufacturing to load an operating system and program the PPC 206.

The power storing module 258 is configured to convert power to recharge one or more rechargeable batteries 302. In this embodiment, the batteries 302 are lithium-ion cells that provide power to operate the PPC 106 allowing it to receive user inputs, transmit control signals to, and charge the IPG 102. The power storing module 258 includes a connector 304 for connecting to a power source, a power protection detection circuit 306 for protecting the PPC from power surges, and linear power supplies 308 for assisting with the electric transfer to charge the batteries 302. As can be seen, the control module 252 aids with the charging and is configured to monitor and send the battery charge level to the user interface 250 for display. The connector 304 connects the PPC, directly or indirectly, to a power source (not shown) such as a conventional wall outlet for receiving electrical current. In some embodiments, the connector 304 comprises a cradle.

The power charging module 256 communicates with the control module 252 and is arranged to magnetically or inductively charge the IPG 102. In the embodiments shown, it is magnetically or inductively coupled to the IPG 102 to charge rechargeable batteries on the IPG 102. The charging module 256 includes components in both the controller-charger portion 200 and the coil portion 202 (FIG. 5). It includes switch boost circuitry 316, a load power monitor 318, an LSK demodulator 320, a ASK modulator 322, a current mode transmitter 324, an ADC 326, and coils 328. As can be seen, the control module 252 aids with the charging and is configured to monitor and send the IPG battery charge level to the user interface 250 for display.

In this embodiment, the coils 328 are disposed in the coil portion 202 and are configured to create magnetic or inductive coupling with components in the IPG 102. Since the coil portion 202 is integrated with the controller-charger portion 200, both operate from a single battery 302. Accordingly, as can be seen by the circuitry, the battery 302 powers the control module 252 and all its associated components. In addition, the battery 302 powers the power charging module 256 for recharging the IPG 102.

Because the coil portion 202 is integrated with the controller-charger portion 200, the control module 252 provides a single control interface and a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

Figure 9:
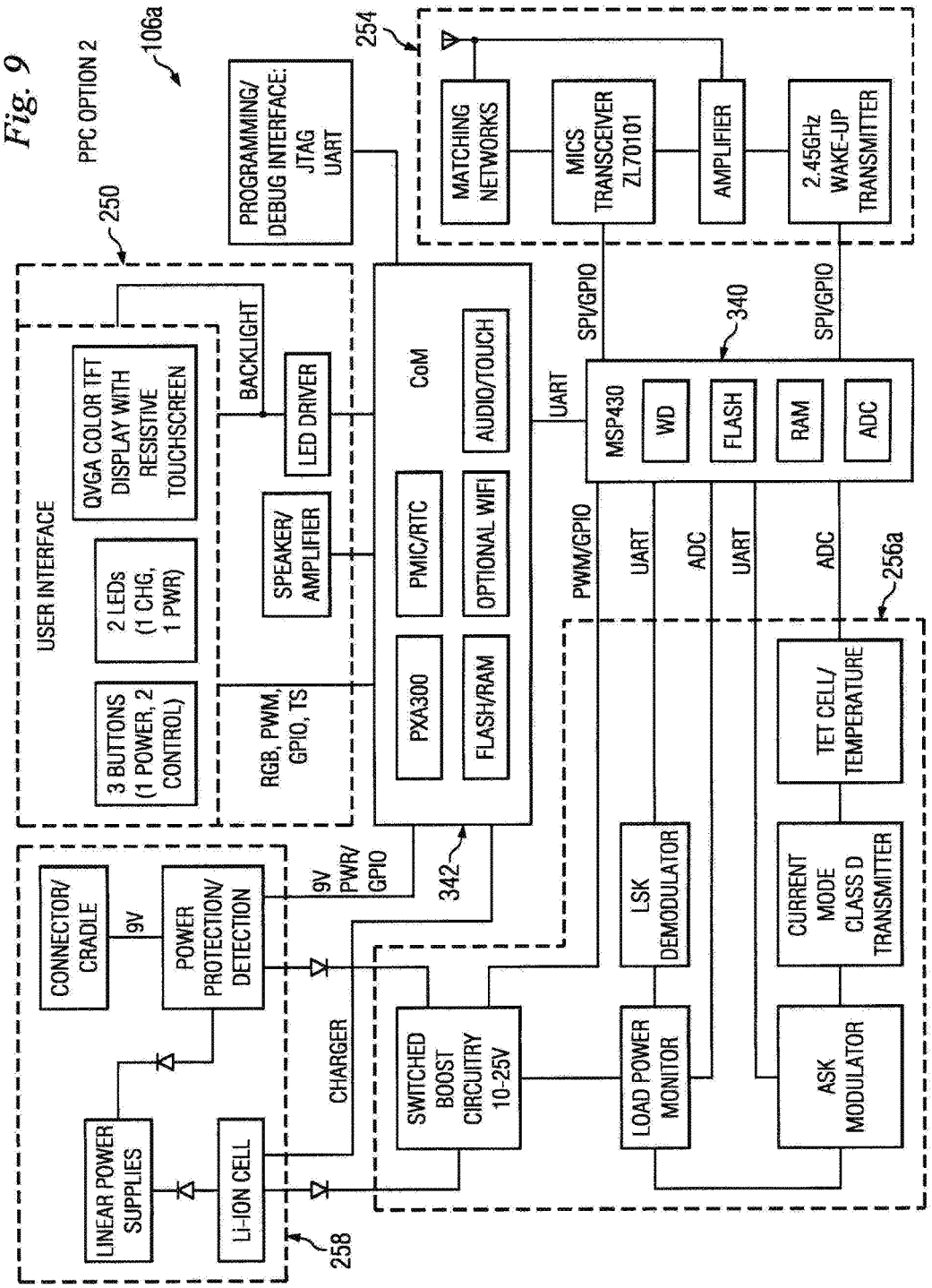
FIG. 9 is block diagram of alternative components of the exemplary patient controller charger of FIGS. 5-7 in accordance with one aspect of the present disclosure.

FIG. 9 shows an alternative embodiment of a PPC, referenced herein by the numeral 106a. In this embodiment, instead of having a single processor in the PPC, the functions of the control module are divided into processors splitting the functions required by the single processor embodiment in FIG. 8. For reference, similar items maintain the same reference numeral.

As can be seen, the PPC 106a includes the user interface 250, the communication module 254, and the power storing module 258. It also includes a power charging module 256a and a control module that in this embodiment includes both a controller 340 and a controller 342. The controller 340 is similar in some ways to the control module 152 in FIG. 4, and the controller 342 is similar in some ways to the control module 252 described in FIG. 8. The controllers 340, 342 have divided the functionality of the PPC into separate portions however. For example, as can be seen, the controller 340 is arranged, and contains instructions for controlling the power charging module 256a and MICS communications module 254, while the controller 342 is arranged and contains instructions for controlling the power storing module 258 and the user interface 250.

As discussed above, the PPC contains all the features available in the pocket controller 104 (stimulation on/off, stimulation program amplitude adjustment, and stimulation program selection). It also includes additional features including, for example, charge IPG battery, individual pulse/area stimulation amplitude adjustment, stimulation program frequency adjustment, individual pulse/area pulse width adjustment, detailed IPG status, detailed PPC status, PPC setup/configuration, PPC battery status indicator, PPC to IPG communication status indicator, and other items.

Figure 10:
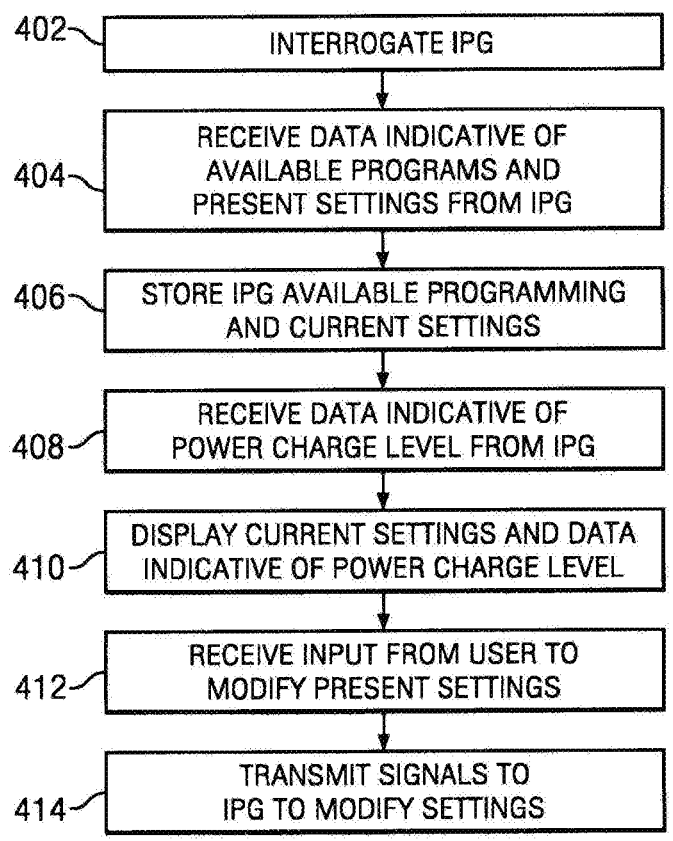
FIG. 10 is a flow chart showing method steps performed by the pocket controller according to one exemplary aspect of the present disclosure.

FIG. 10 is a flow chart showing a method of operation taken by the pocket controller 104 according to one aspect of the present disclosure. The processor 158 and memory 160 contain all the necessary software and programming in order to communicate with the IPG 102 and to receive user inputs performing the available functions of: 1) electrical stimulation on/off, 2) program stimulation amplitude adjustment, and 3) electrical stimulation program selection. In some examples, the control functions of the pocket controller consist only of these functions, while in other embodiments, the control functions contain more or fewer functions, but in all cases is a limited function device having fewer control functional capabilities than the PPC.

When the pocket controller 104 is powered on using the on-off switch 122 and within communication range of the IPG 102, the pocket controller 104 interrogates the IPG 102, as indicated at step 402 in FIG. 10. In response, the IPG 102 transmits to the pocket controller information regarding its current settings including which stimulation programs are available for implementation. As indicated above, some embodiments of the pocket controller communicate only with the IPG 102, and not with the PPC 106. In these embodiments, the pocket controller 104 must receive its data from the IPG. In one example, the information received from the IPG includes the current neurostimulation on-off state, the amplitude setting or level, and the stimulation programs available for implementation.

In this embodiment, the pocket controller 104 may receive data representing a stimulation program identifier uniquely representing each stimulation program that the IPG is capable of carrying out. In FIG. 2, the stimulation program identifier is a numerical number with a "p" as shown at 138. A clinician however, using a clinician programmer or other device, may have only enabled certain stimulation programs on the IPG 102, but not all of the available stimulation programs. In these cases, in response to the interrogation, the pocket controller receives data indicating which stimulation programs are enabled on the IPG 102.

Once received, the pocket controller 104 stores the received data at step 406. At step 408, the pocket controller 104 receives data indicative of the power charge level of the IPG 102, and at step 410, the pocket controller 104 displays the current settings and data indicative of the power charge level. An example of this is shown in FIG. 2, where the pocket controller 104 displays the current on-off state of the electrical stimulation, the amplitude setting, the currently set stimulation program, and the power level of both the IPG 102 and the pocket controller 104.

At step 412, the pocket controller 104 receives an input from a user to modify the current settings. To do this, the pocket controller 104 receives inputs via the adjustment buttons 128a, 128b. In response to the adjustment buttons, the pocket controller scrolls through the available function options and highlights each in turn. The select button 130 allows a user to select the desired highlighted function. Accordingly, when the pocket controller 104 receives a select input via the select button 130, the pocket controller permits modification of the selected function setting using the adjustment buttons 128a, 128b and the select button 130. For example, if the user highlights and selects the stimulation amplitude adjustment function, the pocket controller enters an adjustment mode allowing the user to increase or decrease the amplitude level (shown as a numerical value in FIG. 2) using the adjustment buttons 128a, 128b. Once the desired amplitude level is displayed the user may select it using the select button 130, or alternatively, the controller may automatically enter the displayed value.

In some examples, when the user scrolls to and selects the program function, further inputs by the adjustment buttons 128a, 128b will scroll through the stimulation programs enabled on the IPG, but will not display or allow a user to select stimulation programs that are not enabled on the IPG. For example, if only stimulation programs 1, 5, and 10 out of ten different stimulation programs are enabled, the pocket controller 104 may be programmed to display for selection only stimulation programs 1, 5, and 10, and not display the remaining, non-enabled stimulation programs. Accordingly, the pocket controller may be enabled to only display options available to the user.

In response to receiving an input at the select button 130, the pocket controller 104 transmits data representing the selected adjustment to the IPG 102 at step 414, and the IPG 102 responds by modifying its settings to carry out the command of the pocket controller 104.

Figure 11:
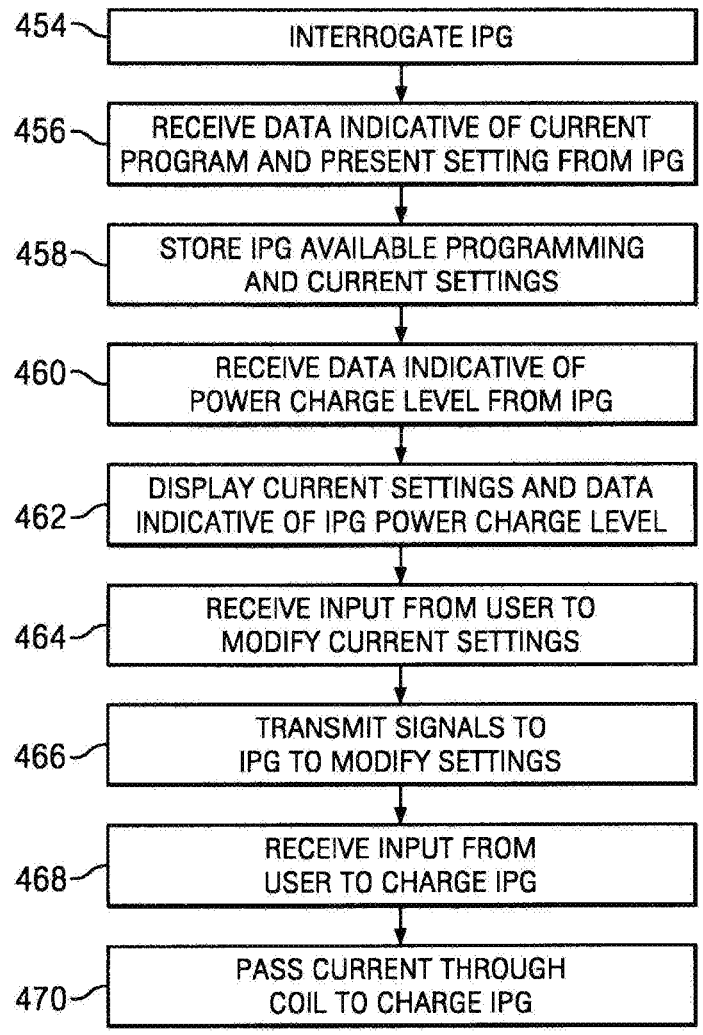
FIG. 11 is a flow chart showing method steps performed by the patient controller charger according to one exemplary aspect of the present disclosure.

FIG. 11 is a flow chart showing a method of operation taken by the PPC 106 according to one aspect of the present disclosure. Although described with reference to PPC 106 in FIG. 8, it should be understood that the method may be performed by any PPC within this scope of this disclosure. The processor 256 and memory 278 contain all the necessary software and programming in order to communicate with the IPG 102, to charge the IPG, and to receive user inputs performing the same control functions as the pocket controller 104, plus additional control functions. For example, these additional control functions performed by the PPC 106 may include charging the IPG battery, adjusting individual pulse/area stimulation amplitude, adjusting stimulation program frequency, adjusting individual pulse/area pulse width, providing detailed IPG status, providing detailed PPC status, enabling PPC setup/configuration, indicating PPC and IPG battery status, displaying PPC to IPG communication status indicator, and other items.

Turning to FIG. 11, when the PPC 106 is powered on using the on-off switch 208 and within communication range of the IPG 102, the PPC 106 interrogates the IPG 102, as indicated at step 454. In response, the IPG 102 transmits to the PPC information regarding its current settings including stimulation programs available for implementation, at step 456. In some embodiments, as described above, the PPC 106 includes a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC.

In some embodiments, the PPC 106 may receive data representing a stimulation program identifier uniquely representing each stimulation program that the IPG is capable of carrying out or programmed to carry out, similar to the operation of the pocket controller 104 above.

The PPC 106 stores the received data at step 458. At step 460, the PPC 106 receives data indicative of the power charge level of the IPG 102, and at step 462, the PPC 106 displays the current settings and data indicative of the power charge level. An example of this is shown in FIG. 5, where the PPC displays the current on-off state of the electrical stimulation, the amplitude setting, the currently set stimulation program, and the power level of both the IPG 102 and the PPC 104, the communication status of the PPC to the IPG. In some embodiments, the PPC 106 displays the current stimulation program frequency, the individual pulse/area pulse width, and other information.

At step 464, the PPC 106 receives an input from a user to modify the current settings. In the exemplary embodiment shown, the PPC 106 includes a touch screen display, and the inputs are received via a user touching an icon displayed on the touch screen display. Once a particular function is selected, the PPC permits modification of the selected function setting using the touch screen. At a step 466, the PPC transmits signals to the IPG to modify the settings and control.

At a step 468, the PPC 106 receives instructions from a user to charge the IPG 102. In response, at step 470, the PPC responds by directing current through the coil 328 for creating an inductive or a magnetic field. Since the coil portion 202 is integrated with the controller-charger portion 200, in the examples shown, both operate from a single battery 302. Accordingly, as can be seen by the circuitry, the battery 302 powers the control module 252 and all its associated components. In addition, the battery 302 powers the power charging module 256 for recharging the IPG 102.

In addition to providing the advantage of a discrete, smaller, functionally limited device, the pocket controller also provides controller redundancy to the patient. Accordingly, the patient is more likely to carry the pocket controller for use, but also serves as a backup to turn off treatments if they become uncomfortable.

The devices, systems, and methods described herein introduce an improved way for controlling and charging an implanted medical device by using a full-featured PPC and a smaller, less intimidating, limited feature, device for everyday use. In addition, because of the redundant nature of the two controllers, the system disclosed herein provides a level of risk management not achieved with a single controller. For example, if one controller malfunctions or is misplaced, the patient still will have the second controller to manage at least the more important and immediate functions of the IPG until the malfunctioning or misplaced controller is replaced. Therefore, the patient can continue with his or her scheduled therapy, modify the stimulation treatment as desired for effectiveness, and control the stimulation in the event that it becomes painful or undesired.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device, comprising:
   a housing having a key-fob-sized form factor;
   electrical circuitry implemented inside the housing, the electrical circuitry including a control module storing instructions and a communication module configured to conduct wireless communications with an implantable pulse generator in response to the instructions received from the control module wherein the implantable pulse generator is configured to generate an electrical stimulation therapy;
   a user display implemented on the housing, the user display being controlled by the control module to simultaneously display a plurality of statuses of the implantable pulse generator;
   a plurality of buttons implemented on the housing, the plurality of buttons being configured to send the instructions, via the communication module, to the implantable pulse generator to control the implantable pulse generator, the device controlling a plurality of implantable pulse generator functions consisting of: turning the electrical stimulation therapy on and off, activating only a subset, but not all, of a plurality of stimulation programs that are stored on the implantable pulse generator, and adjusting an amplitude of a currently-activated stimulation program; and
   an on/off switch located on the housing, the on/off switch being configured to adjustably turn the device on or off.

2. The device of claim 1, wherein the housing has a thickness less than about 1.5 inch, a width less than about 1.5 inch, and a height less than about 3 inches, and wherein the form factor of the housing is configured such that it is attachable to a key ring or a lanyard.

3. The device of claim 1, wherein the plurality of statuses consist of: an amplitude intensity indication, a stimulation program currently being executed by the implantable pulse generator, an on/off status of the implantable pulse generator, and a battery status of the implantable pulse generator, and wherein the user display is further configured to display a battery status of the device.

4. The device of claim 1, wherein the plurality of buttons consist of: an emergency off button for shutting off the electrical stimulation therapy immediately, at least one adjustment button for adjusting the amplitude of the stimulation parameter, and a select button for selecting and activating one of the stimulation programs from the subset of the stimulation programs.

5. The device of claim 1, wherein the communication module includes a medical implant communication service (MICS) transceiver operating in a frequency band ranging from about 402 MHz to about 405 MHz.

6. The device of claim 1, wherein the communication module includes a loop antenna.

7. The device of claim 1, wherein the electrical circuitry further comprises a rechargeable battery and a power storing controller configured to convert power to recharge the rechargeable battery.

8. The device of claim 1, wherein the electrical circuitry further comprises a watch dog circuitry configured to time out when a software running on the electrical circuitry becomes stuck in a loop.

9. The device of claim 1, wherein the device is configured to interrogate the implantable pulse generator in response to the device and the implantable pulse generator being in electronic communication range of each other.

10. The device of claim 1, wherein the device must receive data from the implantable pulse generator.

11. A system, comprising:
    an implantable pulse generator configured to generate electrical pulses for an electrical stimulation therapy; and
    a pocket controller configured to control the implantable pulse generator, wherein the pocket controller includes:
    a housing having a key-fob-sized form factor;
    electrical circuitry implemented inside the housing, the electrical circuitry including a control module storing instructions and a communication module configured to conduct wireless communications with an implantable pulse generator in response to the instructions received from the control module, wherein the implantable pulse generator is configured to generate an electrical stimulation therapy;
    a user display implemented on the housing, the user display being controlled by the control module to simultaneously display a plurality of statuses of the implantable pulse generator;
    a plurality of buttons implemented on the housing, the plurality of buttons being configured to send the instructions, via the communication module, to the implantable pulse generator to control the implantable pulse generator, the pocket controller controlling a plurality of implantable pulse generator functions consisting of: turning the electrical stimulation therapy on and off, activating only a subset, but not all, of a plurality of stimulation programs that are stored on the implantable pulse generator, and adjusting an amplitude of a currently-activated stimulation program; and
    an on/off switch located on the housing, the on/off switch being configured to adjustably turn the pocket controller on or off.

12. The system of claim 11, wherein the form factor of the housing is configured such that it is attachable to a key ring or a lanyard.

13. The system of claim 11, wherein the plurality of statuses consist of: an amplitude intensity indication, a stimulation program currently being executed by the implantable pulse generator, an on/off status of the implantable pulse generator, and a battery status of the implantable pulse generator, and wherein the user display is further configured to display a battery status of the pocket controller.

14. The system of claim 11, wherein the communication module includes a medical implant communication service (MICS) transceiver operating in a frequency band ranging from about 402 MHz to about 405 MHz, and wherein the electrical circuitry further comprises a rechargeable battery, a power storing controller configured to convert power to recharge the rechargeable battery, and a watch dog circuitry configured to time out when a software running on the electrical circuitry becomes stuck in a loop.

15. The system of claim 11, further comprising a patient controller charger (PPC) having a larger form factor than the pocket controller, the PPC offering more programming options than the pocket controller, the PPC containing circuitry configured to electrically charge the implantable pulse generator.

16. The system of claim 11, wherein the pocket controller is configured to interrogate the implantable pulse generator in response to the pocket controller and the implantable pulse generator being in electronic communication range of each other, and wherein the pocket controller must receive data from the implantable pulse generator.

17. A device, comprising:

a housing having a key-fob-sized form factor such that it s attachable to a key ring or a lanyard;

electrical circuitry implemented inside the housing, the electrical circuitry including a control module storing instructions and a communication module configured to conduct wireless communications with an implantable pulse generator that is configured to generate an electrical stimulation therapy in response to the instructions received from the control module;

a user display implemented on the housing, the user display being configured to simultaneously display, based on the instructions received from the control module, a plurality of statuses consisting of: a battery status of the device, a battery status of the implantable pulse generator, a stimulation program currently being executed by the implantable pulse generator, a stimulation amplitude of the stimulation pro ram, and an on/off status of the implantable pulse generator;

a plurality of buttons implemented on the housing, the plurality of buttons being configured to send the instructions, via the communication module, to the implantable pulse generator to control the implantable pulse generator, the device controlling a plurality of implantable pulse generator functions consisting of: turning the electrical stimulation therapy on and off, activating only a subset, but not all, of a plurality of stimulation programs that are stored on the implantable pulse generator, and adjusting an amplitude of a currently-activated stimulation program, wherein the plurality of buttons consist of: an emergency off button for shutting off the electrical stimulation therapy immediately, at least one adjustment button for adjusting the amplitude of the stimulation parameter, and a select button for selecting and activating one of the stimulation programs from the subset of the stimulation programs; and an on/off switch located on the housing, the on/off switch being configured to adjustably turn the device on or off.

18. The device of claim 17, wherein the housing has a thickness less than about 1.5 inch, a width less than about 1.5 inch, and a height less than about 3 inches.

19. The device of claim 17, wherein the communication module includes a loop antenna and a medical implant communication service (MICS) transceiver operating in a frequency band ranging from about 402 MHz to about 405 MHz.

20. The device of claim 17, wherein the device is configured to interrogate the implantable pulse generator in response to the device and the implantable pulse generator being in electronic communication range of each other, and wherein the device must receive data from the implantable pulse generator.

* * * * *

UNITED STATES PATENT AND TRADEMARK OFFICE
CERTIFICATE OF CORRECTION

PATENT NO. : 9,878,165 B2
APPLICATION NO. : 15/270714
DATED : January 30, 2018
INVENTOR(S) : Steven E. Wilder et al.

It is certified that error appears in the above-identified patent and that said Letters Patent is hereby corrected as shown below:

In the Claims

Column 19, Line 20, Claim 17 delete "pro ram" and insert --program--.

Signed and Sealed this
First Day of May, 2018

Andrei Iancu
*Director of the United States Patent and Trademark Office*